United States Patent
Hamlin et al.

(10) Patent No.: US 11,819,412 B2
(45) Date of Patent: Nov. 21, 2023

(54) PENILE PROSTHESES FOR TREATMENT OF ERECTILE DYSFUNCTION

(71) Applicant: Coloplast A/S, Humlebaek (DK)

(72) Inventors: Frederick William Hamlin, Cambridge, MA (US); John J. Allen, Mendota Heights, MN (US); Rahul Dilip Sathe, Needham, MA (US); Neal Poucher, North Oaks, MN (US); Kellie J. Giese, Mounds View, MN (US)

(73) Assignee: Coloplast A/S, Humlebaek (DK)

( * ) Notice: Subject to any disclaimer, the term of this patent is extended or adjusted under 35 U.S.C. 154(b) by 353 days.

(21) Appl. No.: 17/166,062

(22) Filed: Feb. 3, 2021

(65) Prior Publication Data

US 2021/0236288 A1    Aug. 5, 2021

Related U.S. Application Data

(60) Provisional application No. 62/969,668, filed on Feb. 4, 2020.

(51) Int. Cl.
*A61F 2/26* (2006.01)

(52) U.S. Cl.
CPC .......... *A61F 2/26* (2013.01); *A61F 2210/008* (2013.01); *A61F 2250/0058* (2013.01)

(58) Field of Classification Search
CPC ...... A61F 2/26; A61F 2/02; A61F 2250/0058; A61F 2210/008
See application file for complete search history.

(56) References Cited

U.S. PATENT DOCUMENTS

| | | |
|---|---|---|
| 2,764,369 A | 9/1956 | Melton |
| 3,601,923 A | 8/1971 | Rosenberg |
| 4,009,711 A | 3/1977 | Uson |
| 4,342,308 A * | 8/1982 | Trick .......... A61F 2/26 600/40 |
| 4,353,360 A | 10/1982 | Finney et al. |
| 4,360,010 A | 11/1982 | Finney |
| 4,432,357 A | 2/1984 | Pomeranz |
| 4,449,520 A | 5/1984 | Palomar et al. |
| 4,498,466 A | 2/1985 | Pomeranz |
| 4,522,198 A | 6/1985 | Timm et al. |
| 4,564,006 A | 1/1986 | Pomeranz |
| 4,572,168 A | 2/1986 | Fischell |
| 4,594,997 A * | 6/1986 | Hakky .......... A61F 2/26 600/40 |
| 4,625,716 A | 12/1986 | Pomeranz |

(Continued)

FOREIGN PATENT DOCUMENTS

| | | |
|---|---|---|
| CN | 111938873 A | 11/2020 |
| EP | 0051420 A1 | 5/1982 |

(Continued)

*Primary Examiner* — Samuel G Gilbert
(74) *Attorney, Agent, or Firm* — Coloplast Corp., Coloplast A/S; Nick Baumann

(57) ABSTRACT

A penile prosthesis has an energy assembly coupled to a proximal end of a tubular body. The energy assembly has a housing enclosing a piston, a heating element, and a liquid phase change material (PCM) sealed between an interior surface of the housing and the piston. When the heating element heats the liquid PCM to a gaseous state, the piston moves in a distal direction to increase pressure in the tubular body and provide the prosthesis with erection.

24 Claims, 12 Drawing Sheets

(56) References Cited

U.S. PATENT DOCUMENTS

| | | |
|---|---|---|
| 4,664,100 A | 5/1987 | Rudloff |
| 4,671,261 A | 6/1987 | Fischell |
| 4,699,128 A | 10/1987 | Hemmeter |
| 4,782,826 A | 11/1988 | Fogarty |
| 4,881,530 A | 11/1989 | Trick |
| 4,898,158 A | 2/1990 | Daly et al. |
| 4,995,380 A | 2/1991 | Maerzke et al. |
| 5,010,882 A | 4/1991 | Polyak et al. |
| 5,062,417 A | 11/1991 | Cowen |
| 5,069,201 A | 12/1991 | Zinner et al. |
| 5,101,813 A | 4/1992 | Trick |
| 5,112,295 A | 5/1992 | Zinner et al. |
| 5,230,694 A | 7/1993 | Rosenblum |
| 5,840,069 A | 11/1998 | Robinson |
| 6,102,678 A | 8/2000 | Peclat |
| 6,478,773 B1 * | 11/2002 | Gandhi ............... A61B 17/12 604/113 |
| 6,679,832 B1 | 1/2004 | Sultan |
| 7,390,296 B2 | 6/2008 | Mische |
| 8,147,400 B1 | 4/2012 | Daniel |
| 8,152,711 B2 | 4/2012 | Gross |
| 8,343,033 B2 | 1/2013 | Daniel |
| 8,419,612 B2 | 4/2013 | Daniel |
| 8,585,582 B2 | 11/2013 | Daniel |
| 8,636,645 B2 | 1/2014 | Daniel |
| 8,636,646 B2 | 1/2014 | Daniel |
| 8,845,515 B2 | 9/2014 | Daniel |
| 11,051,923 B2 | 7/2021 | Newman et al. |
| 2003/0028076 A1 | 2/2003 | Kuyava et al. |
| 2003/0109771 A1 | 6/2003 | Forsell |
| 2003/0114729 A1 | 6/2003 | Forsell |
| 2003/0135090 A1 | 7/2003 | Forsell |
| 2005/0014993 A1 * | 1/2005 | Mische ............... A61F 2/26 600/40 |
| 2008/0234536 A1 | 9/2008 | Gross |
| 2012/0016187 A1 | 1/2012 | Daniel |
| 2012/0016188 A1 | 1/2012 | Daniel |
| 2012/0136205 A1 | 5/2012 | Aguilera Galeote |
| 2013/0079592 A1 | 3/2013 | Daniel |
| 2014/0221732 A1 * | 8/2014 | Dayton ............... A61M 25/00 604/500 |
| 2019/0321180 A1 * | 10/2019 | Sun ............... A61F 2/26 |

FOREIGN PATENT DOCUMENTS

| | | |
|---|---|---|
| EP | 0182574 A1 | 5/1986 |
| EP | 0978361 A2 | 2/2000 |
| WO | 9741799 A1 | 11/1997 |
| WO | 2007073556 A2 | 6/2007 |
| WO | 2008107716 A1 | 9/2008 |

* cited by examiner

PENILE PROSTHESES FOR TREATMENT OF ERECTILE DYSFUNCTION

BACKGROUND

An implanted penile prosthetic is a proven treatment in relieving erectile dysfunction in men.

A penile prosthesis typically includes two inflatable implants that are implanted in the corpora cavernosa of the penis, a reservoir implanted in the abdomen that communicates with the inflatable implant(s), and a pump, often located in the scrotum, that is employed to move liquid from the reservoir into the inflatable implant(s).

In a typical application, the user squeezes a bulb of the pump multiple times to sequentially transfer liquid from the reservoir to the inflatable implants. Each squeeze of the bulb ejects some liquid into the inflatable implants. The squeezed (compressed) bulb recovers, creating a suction pressure that draws additional liquid out of the reservoir and into the bulb. Subsequent squeezing and recovery of the bulb transfers the liquid collected in the bulb into the inflatable implants, which inflates the inflatable implants to provide the user with an erect penis. The user returns the penis to its flaccid state by selectively activating a deflation mechanism and transferring the liquid from the inflatable implant(s) back into the reservoir.

Patients and surgeons would welcome advances in prostheses addressing erectile dysfunction.

SUMMARY

Several penile prostheses are disclosed, each suited to treat erectile dysfunction, including:

One embodiment of a penile prosthesis includes a plurality of interconnected segments with a juncture formed between each one of the plurality of interconnected segments and an adjacent one of the plurality of interconnected segments, the juncture configured to allow movement between the each one of the plurality of interconnected segments and the adjacent one of the plurality of interconnected segments; a plurality of interconnected rings disposed on an exterior surface of the plurality of interconnected segments with a flex region formed between each one of the plurality of interconnected rings and an adjacent one of the plurality of interconnected rings; a plunger coupled to a proximal end of the plurality of interconnected segments, the plunger is operable to move the plurality of interconnected segments in a distal direction to misalign the flex region with the juncture to provide the prosthesis with axial rigidity adapted for penetrative intercourse; and a lock adapted to maintain a position of the interconnected segments in a displaced distal direction and maintain the axial rigidity of the prosthesis.

One embodiment of a penile prosthesis includes a housing containing an articulated spine formed of a plurality of segments, with the articulated spine adapted to allow a first segment to move relative to a second segment of the articulated spine; a plunger coupled to a proximal end of the articulated spine; and a plurality of rings disposed on an exterior surface of the articulated spine, the plurality of rings adapted to limit movement of the first segment laterally relative to the second segment of the articulated spine; wherein the plunger is operable to move the articulated spine in an axial direction relative to the plurality of rings to prevent lateral movement of the first segment relative to the second segment and provide the prosthesis with axial rigidity adapted for penetrative intercourse.

One embodiment of a penile prosthesis includes a housing coupled to a pressure reservoir by tubing. The housing is adapted for implantation into a corpus cavernosum. The housing includes an expandable tubular portion connected between a proximal tip implantable into a crus penis and a distal tip implantable into a distal cavernosum; a filler sealed inside of the expandable tubular portion, with the filler configured to reduce a volume of liquid contained in the housing calculated to achieve an erection sufficient for penetrative intercourse; and a trigger secured to the housing, with the trigger operable to open a pathway between the pressure reservoir and the expandable tubular portion. When the pressure reservoir contains the volume of liquid and the volume of liquid is pressurized above the housing pressure, movement of the trigger allows a portion of the volume of liquid to flow from the pressure reservoir into the expandable tubular portion.

One embodiment of a penile prosthesis includes a housing coupled to a pressure reservoir by tubing; wherein the housing includes: a tubular film sealed in a liquid-tight arrangement between a proximal tip implantable into a crus penis and a distal tip implantable into a glans penis; and a scaffold nested within the tubular film, where the scaffold forms a sealed compartment inside of the tubular film. The reservoir is adapted to transfer a liquid volume contained inside of the housing from a first location between the tubular film and the scaffold to a second location in which a majority of the liquid volume is contained within the scaffold. The second location of the liquid provides the penile prosthesis with a rigidity sufficient for penetrative intercourse with no net change in the liquid volume contained within the housing.

One embodiment of a penile prosthesis includes an implantable body implantable into a corpus cavernosum of a penis, and a hydrofluorocarbon liquid sealed inside of a portion of the implantable body. The hydrofluorocarbon liquid is adapted to change to a gaseous state to provide the implantable body with a rigidity sufficient for penetrative intercourse.

One embodiment of a penile prosthesis includes a hydrofluorocarbon liquid sealed inside of a portion of an implantable body. The hydrofluorocarbon liquid is adapted to change to a gaseous state and inflate the implantable body. In one embodiment, the hydrofluorocarbon liquid comprises perfluorohexane. In one embodiment, the penile prosthesis further includes a piston contained in a proximal end portion of the implantable body and a filler material contained within a distal end portion of the implantable body. The hydrofluorocarbon liquid in the gaseous state moves the piston in a distal direction to provide the implantable body with a rigidity sufficient for penetrative intercourse.

One embodiment of a penile prosthesis includes a tubular body implantable into a corpus cavernosum of a penis and an energy assembly. The energy assembly is coupled to a proximal end of the tubular body. The energy assembly includes a housing containing piston, a heating element, and a hydrofluorocarbon liquid sealed between an interior surface of the housing and the piston, with the hydrofluorocarbon exposed to the heating element. The heating element is adapted to heat the hydrofluorocarbon liquid to change the hydrofluorocarbon liquid to a gaseous state that expands to move the piston, thus inflating the tubular body and providing the penis with erection.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and advantages of embodiments will be readily appreciated as they become better understood by reference to the following detailed description. The elements of the drawings are not necessarily to scale relative to each other. Like reference numerals designate corresponding similar parts.

DETAILED DESCRIPTION

In the following Detailed Description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used regarding the orientation of the Figure(s) being described. Because components of embodiments can be positioned in several different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the attached claims.

The features of the various exemplary embodiments described in this application may be combined with each other, unless specifically noted otherwise.

The term "proximal" in this application means that part that is situated next to or near the point of attachment or origin or a central point; for example, as located toward a center of the human body. The portion of an implant that is closest to a center of a patient's body is the proximal portion of the implant. For example, the rear tip of a penile implant that is implantable into the crus penis is the proximal end of the implant.

The term "distal" in this application means that part that is situated away from the point of attachment or origin or the central point; for example, as located away from the center of the human body. The glans penis is distal relative to the crus penis of the patient.

End means endmost. A distal end is the furthest endmost location of a distal portion of a thing being described, whereas a proximal end is the nearest endmost location of a proximal portion of the thing being described. The portion next to or adjacent to an end is an end portion. For example, a 12-inch ruler has a center at 6 inches, a first end at zero inches and a second, opposite end at 12 inches, an end portion adjacent to the first end and another end portion adjacent to the second end.

Figure 1:
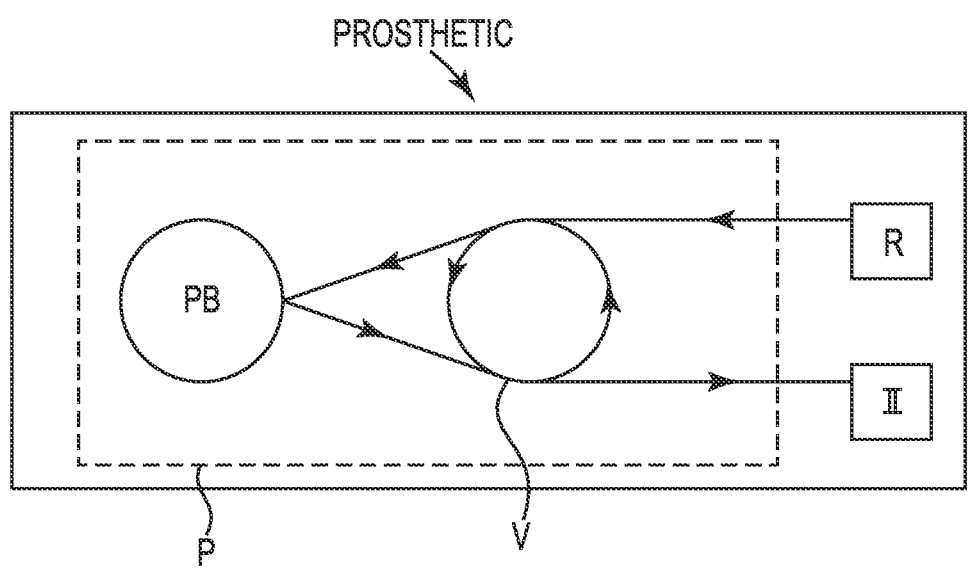
FIG. 1 is a schematic box diagram of a prior art penile prosthesis including a pump bulb coupled between a reservoir and an implant.

FIG. 1 is a schematic box diagram of a known a penile prosthesis. The penile prosthesis includes a pump bulb PB connected with a reservoir R and an inflatable implant II. The pump bulb PB is operable to move liquid from the reservoir R into the inflatable implant II. The penile prosthesis is implantable, and when implanted, is a prosthetic having the implant II, reservoir R, and pump bulb components.

Figure 2:
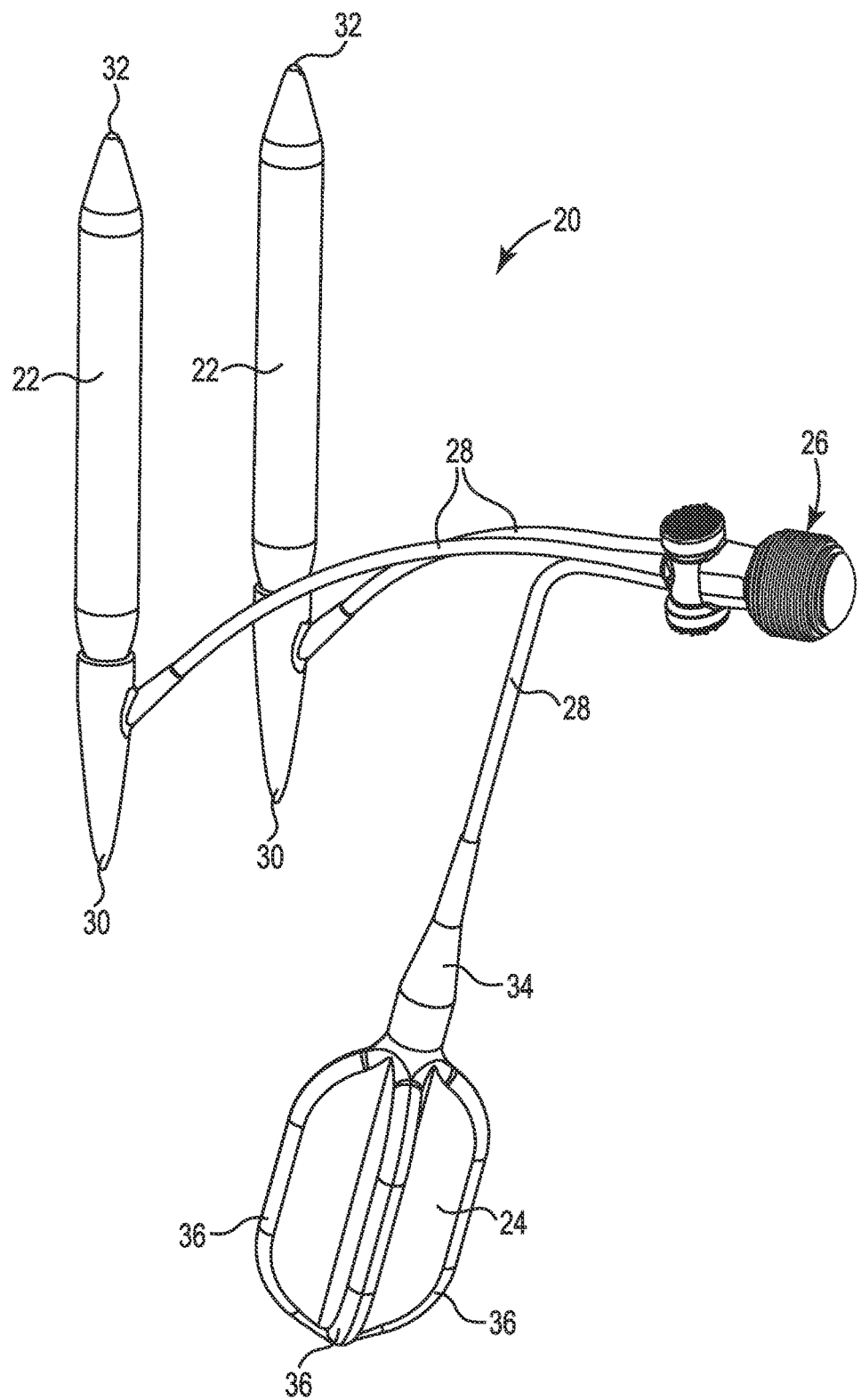
FIG. 2 is a perspective view of one such prior art penile prosthesis consistent with the diagram of FIG. 1.

FIG. 2 is a perspective view of the known penile prosthesis 20 consistent with the box diagram of FIG. 1, for example as assembled by a surgeon during implantation. The penile prosthesis 20 includes inflatable implants 22, a reservoir 24, and a pump 26 connected to the inflatable implants 22 and the reservoir 24, for example by kink resistant tubing 28.

Each of the inflatable implants 22 is sized for implantation into a corpus cavernosum within the penis. Each of the inflatable implants 22 includes a proximal end 30 opposite a distal end 32. During implantation, the proximal end 30 (also called a rear tip) is implanted into the crus of the penis and the distal end 32 is implanted within the glans penis. The inflatable implants 22 are configured to lose rigidity when deflated to provide the penis with a flaccid state, and expand and become rigid when the inflatable implants 22 are inflated with liquid to provide the penis with an erection. As a point of reference, the inflatable implants 22 are illustrated in an inflated state. Suitable material for fabricating the inflatable implants 22 includes silicone, biocompatible polymers such as urethanes, and blends of polymers with urethane, copolymers of urethane, or the like. Suitable inflatable implants are available from Coloplast Corp., Minneapolis, Minn.

The reservoir 24 is sized to maintain a volume of liquid between about 50-300 ml and includes a neck 34 that is smoothly coupled with the kink resistant tubing 28 and at least one collapsible leaf 36, for example in a cloverleaf style. One suitable reservoir 24 is sized to retain approximately 130 mL of liquid and is available from Coloplast Corp., Minneapolis, Minn.

With reference to both FIG. 1 and FIG. 2, the implanted prosthesis 20 provides a prosthetic including the implants 22 implanted in the penis, the reservoir 24 implanted in the abdomen, and the pump 26 implanted in the scrotum. The user is instructed to squeeze the pump 26 multiple times to drive the liquid from the reservoir 24 into the implants 22 to achieve an erection. A release valve is provided, and when activated, the liquid in the implants 22 returns to the reservoir 24.

Figure 3:
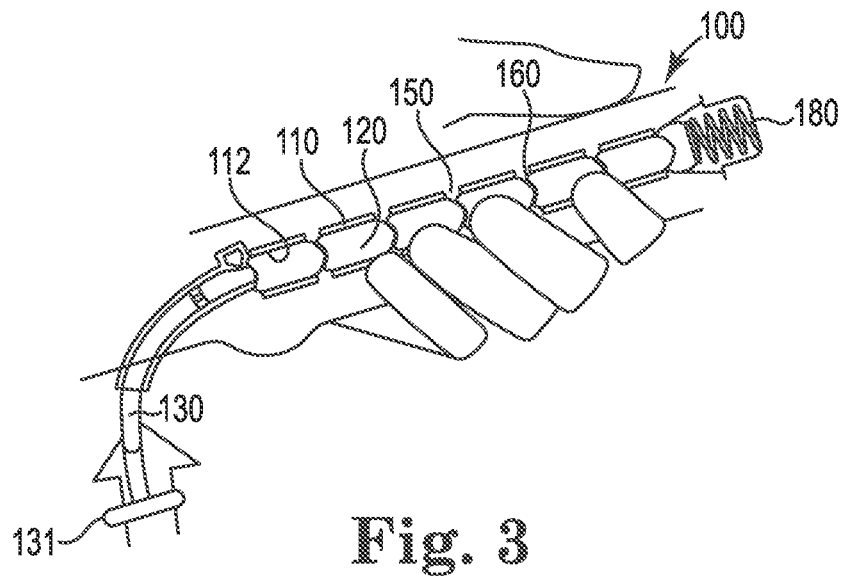
FIG. 3 is a side view of one embodiment of a penile prosthesis.

FIG. 3 is a schematic side view of one embodiment of an implanted penile prosthesis 100 useful in treating erectile dysfunction, where FIG. 3 further illustrates a hand of a user. The prosthesis 100 provides a mechanical solution other than inflation to treat erectile dysfunction by providing a vertebra of interconnected segments that can move and flex until selectively constrained, for example, by annular rings located around the vertebra. The prosthesis is flaccid when the vertebra of connected segments is aligned with spaces in the annular rings (for example, the flex region of each vertebra is aligned with the juncture of the annular rings, as described below in FIG. 4). Displacing the vertebra by about half of a vertebral segment relative to the spaces in the annular rings by operating a plunger (shown by an arrow) will lock the vertebra, resulting in a rigid column of vertebra that provide an erect state for the penis.

The prosthesis 100 includes a plurality of interconnected rings 110 disposed on an exterior surface 112 of a plurality of interconnected segments 120, a plunger 130 coupled to a proximal end of the plurality of interconnected segments 120, and a lock 140 (See FIG. 5) adapted to maintain a position of the interconnected segments 120 in a displaced distal direction. Locking of the segments 120 with the rings 110 provides axial rigidity to the prosthesis 100. The interconnected segments 120, when not constrained by the rings 110, are adapted to move and flex to provide the prosthesis 100 with a natural-feeling flaccid state. The interconnected rings 110 are adapted to interact with the interconnected segments 120 through movement of the plunger 130 to limit the flex or movements of the segments 120, which advantageously provides the prosthesis 100 with a rigidly erect state. The lock 140 allows the user to maintain the prosthesis 100 in the erect state. The rigidly erect state is sufficient to allow penetrative intercourse with the implanted prosthetic 100.

Aspects of the prosthesis 100 that allows both the flaccid and the erect state include the following advantageous configurations. A flex region 150 is formed between each one of the plurality of interconnected rings 110 and an adjacent one of the plurality of interconnected rings 110. A juncture 160 is formed between each interconnected segment 120 and of its neighbouring interconnected segment 120. The juncture 160 provides clearance between segments 120 and a bearing surface between the segments 120, and is configured to allow movement, including rotational movement, between the each one of the plurality of interconnected segments 120 and the adjacent one of the plurality of interconnected segments. The prosthesis 100 allows a first segment 120 to rotate relative to a second segment about a pivot point to facilitate relative movement between the segments.

The plurality of interconnected segments 120 combine to form an articulated spine 170. The plunger 130 is operable to move the plurality of interconnected segments 120, or spine 170, in a distal direction to misalign the flex region 150 with the juncture 160 to provide the prosthesis 100 with axial rigidity adapted for penetrative intercourse. In one embodiment, the plunger 130 is operable to move the rings 110 to misalign the flex region 150 with the juncture 160 to provide the prosthesis 100 with axial rigidity adapted for penetrative intercourse. To return the prosthesis 100 to its flaccid state, the user releases the lock 140 and a biased spring 180 forces the rings 110 back into alignment with the segments 120, which returns the prosthesis to its flaccid state.

Figure 4:
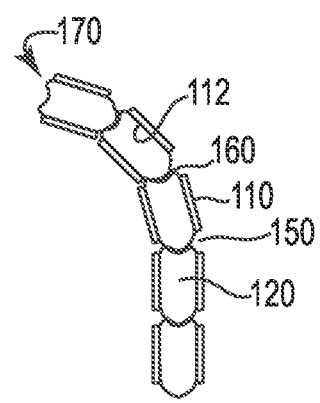
FIG. 4 is a side view of one embodiment of an articulated spine having interconnected segments employed in the prosthesis of FIG. 3.

FIG. 4 is a side view of one embodiment of the articulated spine 170 formed by the interconnected segments 120. The articulated spine 170 is typically housed in a polymeric, flexible implantable cylindrical tube or similar such container, which is not illustrated in FIG. 4. The articulated segments 120 are suitably interconnected by a metal wire strand, a polymeric string, a synthetic string, or a natural fiber string. The articulated segments 120 are not constrained by the aligned rings 100 and the prosthesis 100 is flaccid. The plurality of interconnected rings 110 (rings 110) are disposed around the plurality of interconnected segments 120 (segments 120), and the plunger 130 is coupled to the proximal end of the segments 120. The articulated spine 170 is moveable relative to the rings 110 to shift an alignment (or a misalignment) between the flex regions 150 of the rings 110 and the junctures 160 of the segments 120. FIG. 4 shows a flex region 150 is aligned with the juncture 160, which allows the segments 120 to move since the junctures 160 between the segments 120 are not constrained. This movement allows the articulated spine 170 to bend. The movement of the segments 120 when the flex region 150 is aligned with the juncture 160 includes up/down movement (pitch) of the segments relative to each other and left/right movement (yaw) of the segments relative to each other. The segments 120 are interconnected one to another such that axial movement of the segments 120 away from each other is constrained or prevented.

Figure 5:
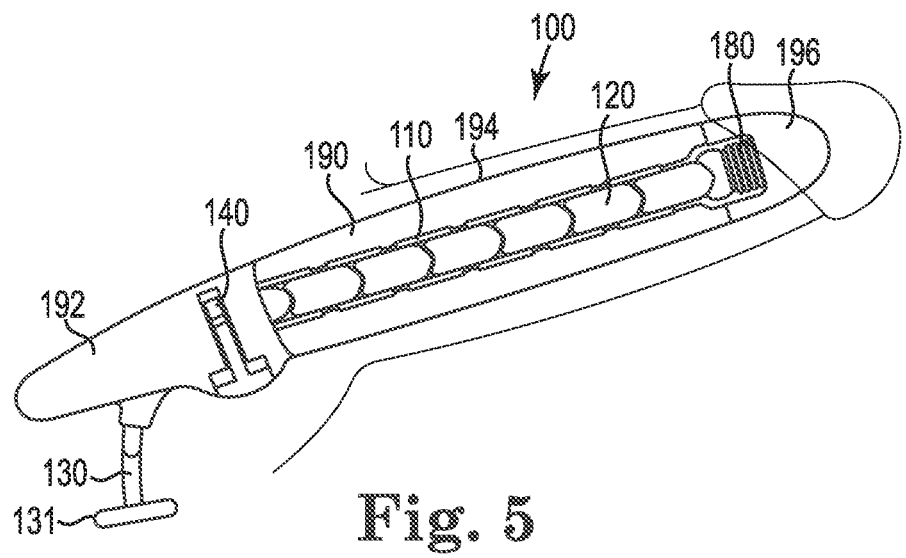
FIG. 5 is a schematic side view of the prosthesis of FIG. 3 in an erect state when implanted in a penis.

FIG. 5 is a schematic view of the prosthesis 100 contained in a housing 190 and implanted in a penis with the rings 110 holding the segments 120 in a laterally and axially rigid configuration. The housing 190 includes a proximal rear tip 192, a flexible body 194, and a distal tip 196. The plunger 130 is coupled with the proximal rear tip 192 and the return spring 180 is in the distal tip 196. The body 194 is sealed to the rear tip 192 and the distal tip 196, which allows the body 194 to advantageously hold liquid or other filler material that gives the implant a natural girth and feel.

The plunger 130 is coupled to the proximal end of the articulated spine 170 to move the segments 120 into or out of alignment with the rings 110. When the plunger 130 is pushed in a distal direction, the segments 120 move distal relative to the rings 110, and this movement misaligns the flex regions 150 (FIG. 4) with the junctures 160 along the articulated spine 170 (FIG. 4). In this case, the rings 110 become positioned over the juncture 160, which prevents the movement of the segments 120 and provides the prosthesis 100 with axial rigidity adapted for penetrative intercourse. The lock 140 is provided to hold the articulated spine 170 in the forward (or distal) location, which locks or maintains the prosthesis 100 in an erect state. One suitable location for the plunger when implanted is inferior to the shaft of the penis near the perineum, although other locations are possible.

The articulated spine 170 is immersed in a fluid, with the fluid dispersed around the segments 120 or the flex regions 150 and rings 110. When the plunger 130 is pushed in the distal direction, the segments 120 move distal relative to the rings 110, and the fluid that was held within the junctures 160 becomes displaced away from the segments 120 to a location outside of the rings 110. The fluid that is displaced is outside of the flex region 150. In the flaccid state, the flex region 150 forms a depression into the junctures 160 and fluid fills this depression. Shifting of the segments 120 forces the flex region 150 outward along with the fluid that had filled the depression. Under one theory of operation, the displacement of the fluid in the prosthesis 100 can contribute to an advantageous girth enhancement for the device when in the erect state. Suitable fluids include saline, silicone oils, hydrocolloid particles, gels, and the like.

In one embodiment, the user releases the lock 140 and manually forces the rings 110 back into alignment with the segments 120, which returns the prosthesis to its flaccid state. The lock 140 operates as a push release button that allows the erect prosthesis 100 to return to its flaccid state. Another possible embodiment uses the elevated fluid pressure, generated when the segments 120 were shifted distally, to force the segments 120 to shift proximally.

In one embodiment, the user releases the lock 140 and a biased spring 180 forces the rings 110 back into alignment with the segments 120, which returns the prosthesis to its flaccid state. The spring 180 is compressed when the prosthesis 100 is in the erect state.

The flexible body 194 is preferably a thin-walled polymeric film, such as a polyurethane thin film. The flexible body 194 is an expandable tubular structure connected between the rear tip 192 and the distal tip 196. One suitable flexible body 194 is provided by the inflatable penile prosthesis cylinder sold under the trademark Titan® by Coloplast Corp., Minneapolis, Minn.

Figure 6:
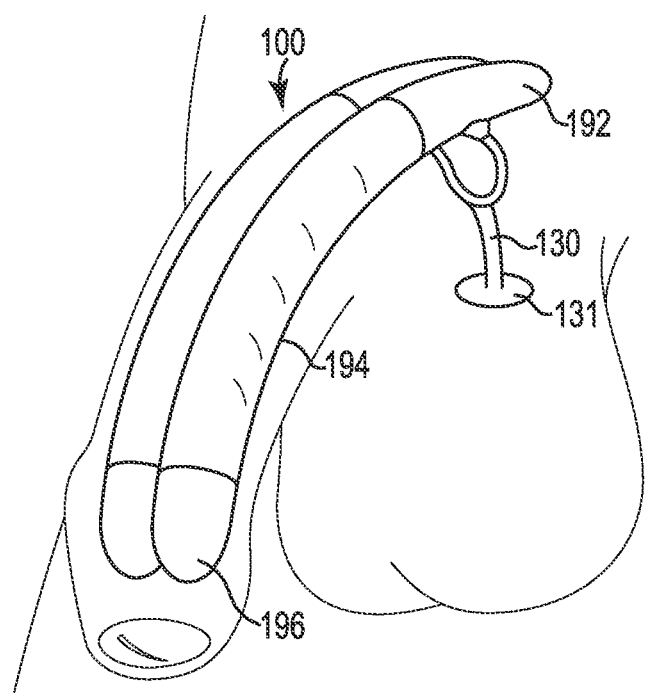
FIG. 6 is a schematic side view of the prosthesis of FIG. 3 in a flaccid state when implanted in a penis.

FIG. 6 is a perspective view of one embodiment of the prosthesis 100 employed to treat erectile dysfunction. The prosthesis 100 is adapted for implantation into a dilated corpus cavernosum of a penis, and as such, it is useful to provide each cavernosum with one of the prostheses 100. In one embodiment, two such prostheses 100 are provided, with a first prosthesis implanted in a left cavernosum and a second prosthesis implanted in a right cavernosum. Two mutually coupled plungers 130 are provided, one each for each prosthesis 100. Movement of a plunger button 131 pushes both plungers 130 in the distal direction to drive both prostheses 100 to the erect state.

The prosthesis 100 is an implant II having articulated segments associated with articulated rings, with the segments and the rings surrounded by liquid, the components of which are adapted to allow the prosthesis 100 to transition between the flaccid and erect states. Maintaining all the components in a single device implantable into a cavernosum allows the implantation procedure to have fewer steps than a procedure for implanting the device (cylinders, reservoir, pump, and tubing) of FIG. 2. The fluid surrounds both the articulated segments AS and the articulated rings AR. The plunger P is coupled with the articulated segments AS. Unlike the prior art inflatable penile implant (IPP) of FIG. 2, the prosthesis does not require a separately implanted reservoir or a separately implanted pump coupled to the penile implant. The prosthesis 100 is less complex than the prior art IPP (FIG. 1), with fewer parts, which translates to a less complex implantation procedure.

One embodiment of the penile prosthesis 100 includes a plunger coupled to interconnected segments and interconnected rings disposed around the interconnected segments. The plurality of interconnected segments has a juncture formed between each one of the plurality of interconnected segments and an adjacent one of the plurality of interconnected segments. The juncture is configured to allow lateral movement between the each one of the plurality of interconnected segments and the adjacent one of the plurality of interconnected segments. The plurality of interconnected rings is disposed on an exterior surface of the plurality of interconnected segments with a flex region formed between each one of the plurality of interconnected rings and an adjacent one of the plurality of interconnected rings. The plunger is coupled to a proximal end of the plurality of interconnected segments. The plunger is operable to move the plurality of interconnected segments in a distal direction to misalign the flex region with the juncture to provide the prosthesis with axial rigidity adapted for penetrative intercourse. A lock is provided to maintain a position of the interconnected segments in a displaced distal direction and maintain the axial rigidity of the prosthesis.

One embodiment of the penile prosthesis 100 includes a housing containing an articulated spine, a plunger coupled to the articulated spine, and rings disposed around the spine. The housing contains the articulated spine that is formed of a plurality of segments, with the articulated spine adapted to allow a first segment to move laterally relative to a second segment of the articulated spine. The plunger is coupled to a proximal end of the articulated spine. A plurality of rings is disposed on an exterior surface of the articulated spine. The plurality of rings is adapted to limit movement of the first segment laterally relative to the second segment of the articulated spine. The plunger is operable to move the articulated spine in an axial direction relative to the plurality of rings to prevent lateral movement of the first segment relative to the second segment and provide the prosthesis with axial rigidity adapted for penetrative intercourse.

Figure 7:
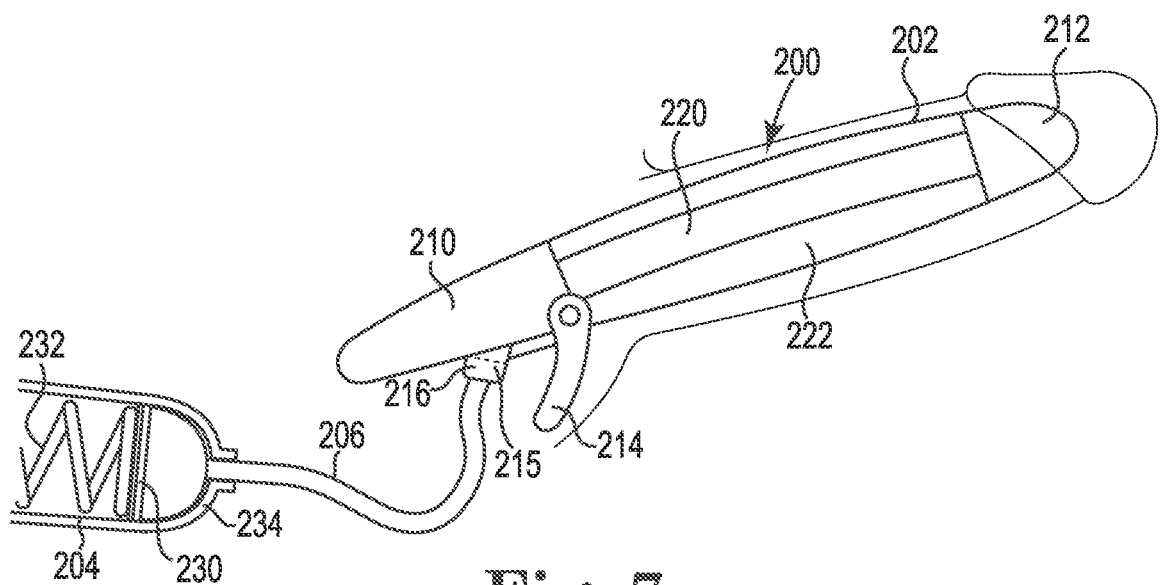
FIG. 7 is a schematic side view of one embodiment of an implanted penile prosthetic in an erect state.

FIG. 7 is a schematic side view of one embodiment of an implanted penile prosthetic 200 in an erect state. The prosthetic 200 includes a housing 202 coupled to a pressure reservoir 204, or chamber 204, by tubing 206.

The housing 202 extends between a proximal rear tip 210 and a distal tip 212, and includes a trigger 214 that is employed to activate a valve assembly 215 in a well 216. In one embodiment, the housing 202 includes a liquid sparing element, or a filler 220, sealed inside of the housing. The filler 220 advantageously reduces the amount of liquid 222 employed by the implant to achieve a sufficient erection for penetrative intercourse.

The housing 202 is preferably a thin-walled polymeric film, such as a polyurethane thin film. The housing 202 is an expandable tubular structure connected between the rear tip 210 and the distal tip 212. One suitable housing 202 is provided by the inflatable penile prosthesis cylinder sold under the trademark Titan® by Coloplast Corp., Minneapolis, Minn.

One suitable filler is an open cell foam, such as a polyurethane open cell foam. Other flexible fillers are acceptable, such as a gel-filled pocket or a liquid-filled pocket internalized inside of the housing 202.

The chamber 204 is configured to retain the liquid 222 in a pressurized state. The chamber 204 includes a piston 230 and a spring 232 retained inside of a wall 234. The tubing 206 is connected through the wall 234 of the chamber 204 and forms a flow path for the liquid 222 to move between the housing 202 and the chamber 204. In one embodiment, the chamber 204 is implantable in a perineal space. Other suitable locations for implantation of the chamber 204 include within the pelvis or in the abdomen, based on the preference of the surgeon. In another embodiment, the strain energy storage is achieved with an expandable polymeric membrane, for example, a balloon.

Figure 8:
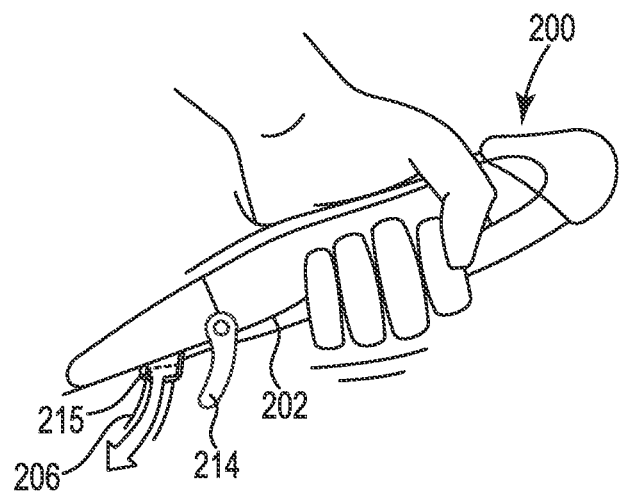
FIG. 8 is a schematic side view of a user deflating the implanted penile prosthetic in FIG. 7.

FIG. 8 is a schematic side view of a user deflating the implanted penile prosthetic 200. The user is instructed by instructions for use (provided with the packaged product) to squeeze the erect implant to increase the pressure inside of the housing 202. When the pressure in the housing 202 reaches a selected break pressure (for example, in a range from about 10 psi to 25 psi) applied on the distal side of the valve 215, the valve assembly 215 opens, and the liquid 222 flows through the tubing 206 and into the chamber 204. In one embodiment, the liquid 222 is pressurized in the chamber 204 through repeated squeezing of the housing 202. Alternatively, the liquid 222 is pressurized in the chamber 204 through a separate energy source such as a pump located in the tubing 206 or the chamber 204. In any regard, the liquid 222 in the chamber is maintained at a pressure above a range from about 10 psi to about 25 psi. Alternatively, the user cracks open the valve 215 using the trigger 214 and manually squeezes the liquid into the pressure chamber 204.

Figure 9:
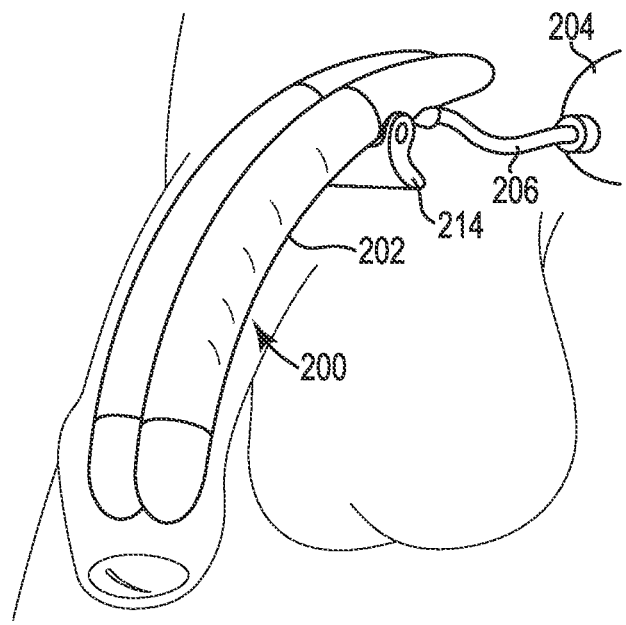
FIG. 9 is a schematic view of the flaccid implanted penile prosthetic after deflation.

FIG. 9 is a side view of the flaccid implanted penile prosthetic 200 after deflation by the user. The housing 202 is flaccid and the liquid in the chamber 204 is maintained at an elevated pressure, for example, a pressure between about 10-25 psi.

Figure 10:
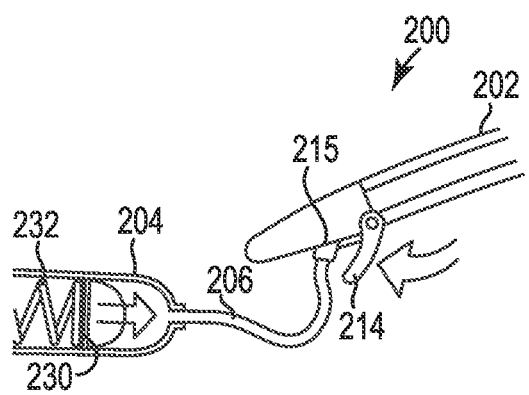
FIG. 10 is a side view of the penile prosthesis transitioning to the erect state illustrated in FIG. 7.

FIG. 10 is a side view of the penile prosthesis 200 transitioning to the erect state that is illustrated in FIG. 7. The user is instructed in the instructions for use provided with the device to stroke a length of the housing 202 from the distal tip 212 toward the proximal rear tip 210, and in so doing, to displace the trigger 214. Displacement of the trigger 214 releases some of the pressurized liquid 222 stored in the chamber 204 through the tubing 206 and into the housing 202. The liquid 222 leaves the chamber 204 at a pressure range between 10-25 psi and enters the housing 202, where the expanded volume reduces the pressure in the housing to a pressure lower than the initial pressure in the chamber 204 before the fluid was released. The filler 220 occupies some volume in the housing 202, consequently, a volume of liquid that is smaller than the total volume of the housing will sufficiently fill the housing 202 and provide the prosthetic 200 with an erection. Repeated movement of the trigger 214 will consecutively eject liquid 222 from the chamber 204 into the housing 202 until a desired firmness of the erect state is achieved. In one embodiment, the user maintains the trigger 214 in an activated state to allow the flow to re-pressurize in one go.

The penile prosthesis 200 includes a housing coupled to a pressure reservoir by tubing. The housing is adapted for implantation into a corpus cavernosum. The housing includes an expandable tubular portion connected between a proximal tip implantable into a crus penis and a distal tip implantable into a glans penis; a filler sealed inside of the expandable tubular portion, with the filler configured to reduce a volume of liquid contained in the housing calculated to achieve an erection sufficient for penetrative intercourse; and a trigger secured to the housing, with the trigger operable to open a pathway between the pressure reservoir and the expandable tubular portion. When the pressure reservoir contains the volume of liquid and the volume of liquid is pressurized above the pressure in the housing 202, movement of the trigger allows a portion of the volume of liquid to flow from the pressure reservoir into the expandable tubular portion.

Figure 11:
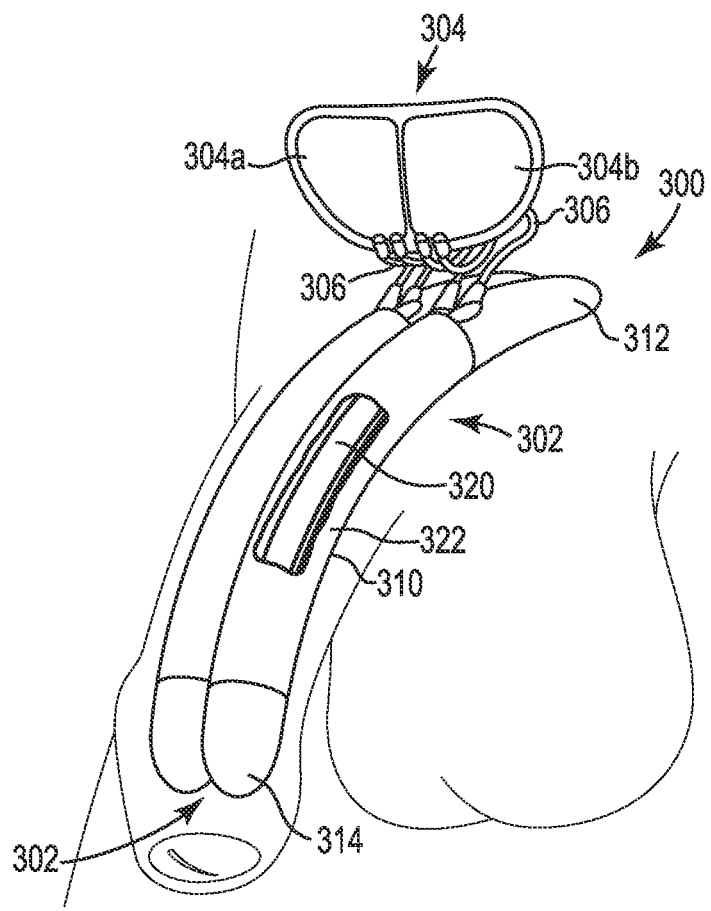
FIG. 11 is a perspective view of one embodiment of an implanted penile prosthesis in a flaccid state.

FIG. 11 is a perspective view of one embodiment of an implanted penile prosthesis 300 in a flaccid state. The penile prosthesis 300 provides a two-piece prosthesis that has an improved flaccid-to-rigid dynamic range.

Figure 12:
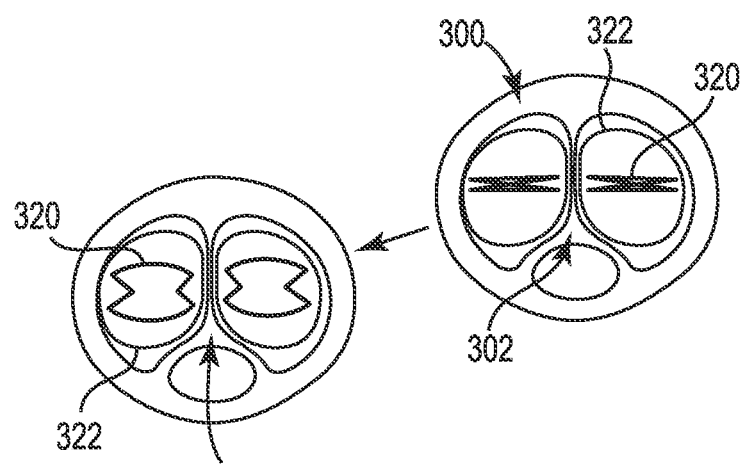
FIG. 12 is a cross-sectional view of FIG. 11.

FIG. 12 is a cross-sectional view of the implanted penile prosthesis 300 in a flaccid state transitioning to an erect state.

Figure 13:
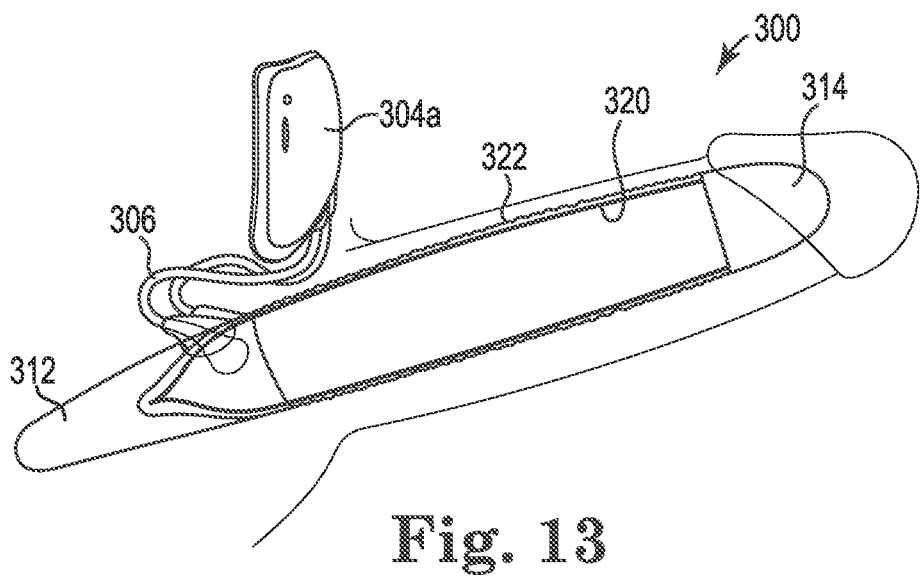
FIG. 13 is a side view of the implanted penile prosthesis of FIG. 11 in an erect state.
Figure 14:
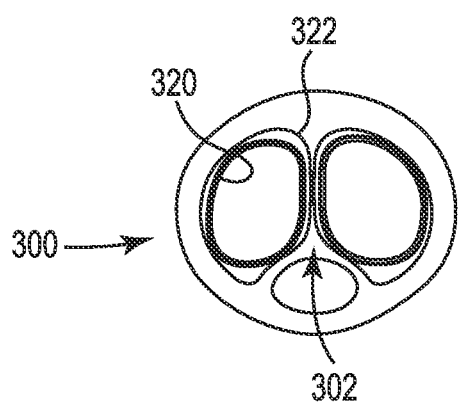
FIG. 14 is a cross-sectional view of FIG. 13.

FIG. 13 is a side view of the implanted penile prosthesis 300 in an erect state, where FIG. 14 is a cross-sectional view of FIG. 13.

The penile prosthesis 300 (FIGS. 11-14) includes a pair of penile implants 302 coupled to a pump assembly 304 by tubing 306. The pump assembly 304 is illustrated in a pre-pubic location, although other implant locations are possible based upon surgeon preference or experience. In one embodiment, repeatedly pressing on the right side 304a of the pump assembly 304 operates to move fluid from the reservoir into the implants 302 for inflation, and pressing on the left side 304b of the pump assembly 304 operates to move fluid from the implants 302 back into the reservoir for deflation.

Each of the pair of penile implants 302 includes a body 310 extending between a rear proximal tip 312 and a distal tip 314. One embodiment of the body 310 is cylindrical in shape, and the body 310 is inflatable. When the body 310 is filled with fluid it becomes oversized and yet remains flaccid. The rear proximal tip 312 is configured for implantation into the crus penis and the distal tip 314 is sized for implantation in the glans penis. The body 310 contains a fluid that surrounds a scaffold 320, where the exterior surface of the body 310 is formed by a thin-walled and flexible polymeric film 322. In one embodiment, the film 322 optionally has a corrugated structure. The scaffold 320 is nested inside of the body 310 and includes extruded bellows that are reinforced, and in one example the bellows portion of the scaffold 320 is fiber-reinforced. The scaffold 320 is configured to expand from the centerline of the implants 302 toward the inner surface of the wall formed by the film 322 when the fluid is moved from the outside of the scaffold 320 to inside of the scaffold 320. The scaffold 320 doesn't necessarily expand all the way out to the film 322. The scaffold 320 is sized to have a lower fluid capacity than the film 322, such that when fluid is transferred, the fluid is under higher pressure than when the fluid was outside of 322. In embodiments, the film 322 doesn't need to have a wavy structure; the film 322 could also be a smaller diameter cylinder that expands when filled. The amount of pressure achieved when filled can be controlled by the material and wall thickness of the cylinder.

The thin-walled and flexible polymeric film 322 contains the fluid and provides the implants 302 with excellent flaccidity when the prosthesis is not inflated. In one embodiment, pressing on the right side 304a of the pump assembly 304 operates to move fluid from between the body 310 and the scaffold 320 to a location where the fluid is inside the scaffold 320, which inflates the implant. Pressing on the left side 304b of the pump assembly 304 operates to move fluid out of the scaffold 320 and back into the location between the body 310 and the scaffold 320, which operates to deflate the implant.

Movement of the fluid into the scaffold 320 initiates a dramatic increase in its second moment of area, which allows the implants 302 to move between the flaccid state and the rigid state without compromising either state. In combination, the scaffold 320 and the thin-walled, flexible polymeric film 322 with the corrugated structure offers very good flaccidity in the deflated state and very good rigidity in the inflated state.

The movement of the fluid, for example saline, from a location between the scaffold 320 and the thin-walled and flexible polymeric film 322 to inside of the scaffold 320 increases the rigidity of the implants 302 with no net increase in the volume of the saline contained in the implant inside of the corpora cavernosum. In one embodiment, the scaffold 320 is a cigar-shaped cylinder placed inside of a larger cigar-shaped body 310. Thus, the diameter of the scaffold 320 is less than the diameter of the body 310. Since the volume of the liquid or saline is fixed by the size of the body 310, when the liquid is moved into the relatively smaller diameter of the scaffold 320, the scaffold 320 becomes pressurized and expands. The film 322 is not intended to be pressurized or under stress. The pressure of the liquid in the body 310 and inside of the film 322 is constant, and is approximately zero psi. The transfer of the fluid into the scaffold 320 will expand the scaffold 320 to provide the implants 302 with an erection, however, the film 322 is not pressurized or stressed. The film 322 has a low bending stiffness, which makes it very flexible and well suited to providing the user with a natural flaccid and a natural erect state of the penis.

The penile prosthesis 300 includes a housing coupled to a pressure reservoir by tubing; wherein the housing includes: a tubular film sealed in a liquid-tight arrangement between a proximal tip implantable into a crus penis and a distal tip implantable into a glans penis; and a scaffold nested within the tubular film, where the scaffold forms a sealed compartment inside of the tubular film. The reservoir is adapted to transfer a liquid volume contained inside of the housing from a first location between the tubular film and the scaffold to a second location in which a majority of the liquid volume is contained within the scaffold. The second location of the liquid provides the penile prosthesis with a rigidity sufficient for penetrative intercourse with no net change in the liquid volume contained within the housing.

One embodiment provides a penile prosthesis comprising a tubular body comprising a first portion coupled to a second portion, where the first portion contains a perfluorocarbon liquid and a heat source, and the second portion contains a liquid and a filler. The heat source contained in the first portion is adapted to change a phase of the perfluorocarbon liquid to a gas to thus pressurize the liquid and the filler in the second portion to provide the penile prosthesis with rigidity suitable for an erection.

One embodiment provides a multi-stroke pump that is configured to cycle multiple times to complete fluid transfer from a reservoir to a penile cylinder. The multi-stroke pump includes an energy assembly that is adapted to cycle to inflate the prosthesis and create an erection. One example of the cycle includes heating a liquid phase change material (PCM) with a heating element to change its state to a gaseous state. This results in expansion of an expansion element, which could be a piston or a bellows. The expansion element expands into a chamber that contains a system liquid, and this expansion causes the system liquid to be displaced out from the chamber and into the prosthesis through an outlet. After full expansion of the expansion element, the heating element is turned off and the PCM begins to cool. Dissipation of heat causes condensation of the PCM transitioning it back to its fluid state. During cooling, the expansion element contracts, creating a vacuum in the chamber and drawing additional system liquid out from a reservoir and into the chamber. Repetition of this cycle operates to transfer system liquid from the reservoir into the prosthesis.

A variety of embodiments of a penile prosthesis are disclosed.

In one embodiment, a penile prosthesis is implantable into a corpus cavernosum of a penis, the penile prosthesis comprising: an energy assembly contained within the penile prosthesis, the energy assembly comprising a heating element and a liquid phase change material (PCM) sealed within an expansion element, with the liquid PCM exposed to the heating element; and a distal portion coupled with the energy assembly, with the distal portion containing a liquid; wherein the heating element is adapted to heat the liquid PCM to a gaseous state that expands to move the expansion element in a distal direction, thus increasing a pressure in the liquid in the distal portion thus providing the penile prosthesis with erection.

An aspect of the above embodiment includes where the heating element comprises an electric coil that is coupled to a battery.

An aspect of the above embodiment includes where the liquid PCM is perfluorohexane $C_6F_{14}$.

An aspect of the above embodiment includes where the liquid PCM has a boiling point of 59 C.

An aspect of the above embodiment includes where the liquid PCM has a 15 psig vapor temperature of 78 C.

An aspect of the above embodiment includes where the expansion element is a piston.

An aspect of the above embodiment further includes a piston stop adapted to limit travel of the piston in the distal direction.

An aspect of the above embodiment further includes a lock-out adapted to retain the piston at an expanded distal position to maintain the erection as the hydrofluorocarbon gaseous state returns to the hydrofluorocarbon liquid.

An aspect of the above embodiment includes where the expansion element is a bellows.

An aspect of the above embodiment includes where the distal portion is a sealed distal portion sealed to contain a filler immersed in the liquid, and movement of the expansion element in the distal direction pushes into the sealed distal portion to increase the pressure in the liquid to provide the penile prosthesis with erection.

An aspect of the above embodiment includes where the distal portion is a sealed distal portion sealed to contain a gel suspended in the liquid, and movement of the expansion element in the distal direction pushes into the sealed distal portion to increase the pressure in the liquid to provide the penile prosthesis with erection.

An aspect of the above embodiment further includes where a rigid first portion is connected to the distal portion, and the energy assembly is contained inside of the rigid first portion of the penile prosthesis.

An aspect of the above embodiment includes where the energy assembly is contained inside of a chamber, with the chamber containing a first volume of system liquid, and the expansion element communicates with the first volume of system liquid, with the penile prosthesis further comprising: a reservoir coupled to the chamber, with the reservoir containing a second volume of system liquid; and a port communicating between the chamber and the distal portion; wherein movement of the expansion element in the distal direction displaces a portion of the first volume of system liquid through the port and into the distal portion to pressurize the liquid in the distal portion, thus providing the penile prosthesis with erection.

An aspect of the above embodiment includes where a lateral dimension of the chamber is approximately equal to a diameter of the expansion element.

An aspect of the above embodiment further includes where a coil is placed around the expansion element, with the coil adapted to dissipate heat generated by the energy assembly.

Another embodiment provides a penile prosthesis comprising: a tubular body comprising a distal portion coupled to a proximal portion, where the distal portion contains a fluid and the proximal portion comprises an energy assembly; wherein the energy assembly encloses a heating element and a hydrofluorocarbon liquid sealed inside of an expansion element, with the hydrofluorocarbon exposed to the heating element; wherein changing a state of the hydrofluorocarbon liquid to a gaseous state expands the expansion element in a distal direction to pressurize the fluid in the distal portion, thus providing the penile prosthesis with erection.

An aspect of the above embodiment includes where the expansion element is a piston and the distal portion is sealed with a barrier between the proximal portion and the distal portion, with the fluid sealed inside of the distal portion; wherein, expansion of the expansion element pushes the piston into the barrier to pressurize the fluid sealed in the distal portion.

An aspect of the above embodiment includes where the expansion element is a bellows and the proximal portion comprises a chamber containing system liquid that surrounds the bellows, with the penile prosthesis further comprising: a reservoir coupled to the chamber; and a port communicating between the chamber and the distal portion; wherein expansion of the expansion element in the distal direction displaces a portion of the system liquid out of the chamber and through the port and into the distal portion to pressurize the fluid in the distal portion, thus providing the penile prosthesis with erection.

An aspect of the above embodiment further includes where a battery is electrically coupled to the heating element.

An aspect of the above embodiment includes where the distal portion is sealed to contain a filler in the fluid, and the filler is configured to increase a girth of the distal portion when the penile prosthesis is flaccid.

Figure 15:
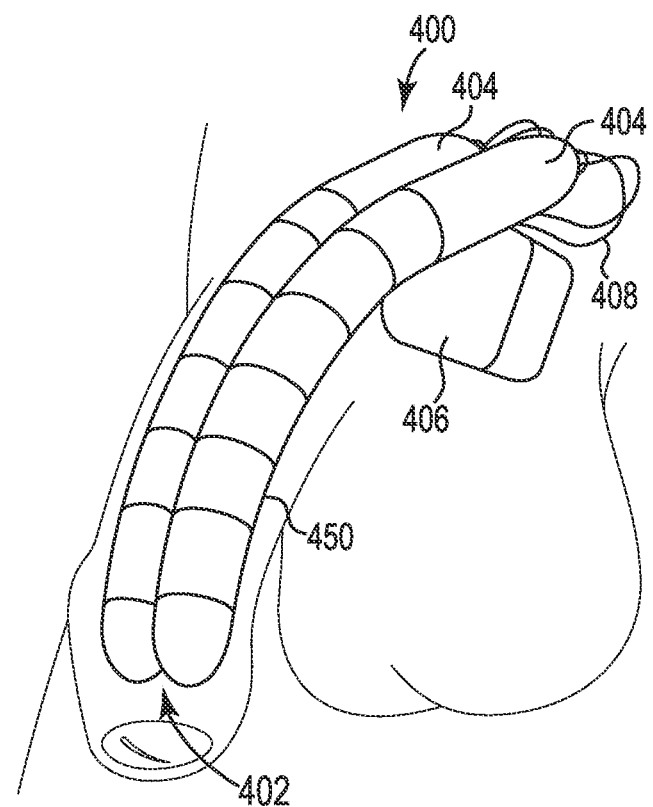
FIG. 15 is a perspective view of one embodiment of an implanted penile prosthesis in a flaccid state.
Figure 16:
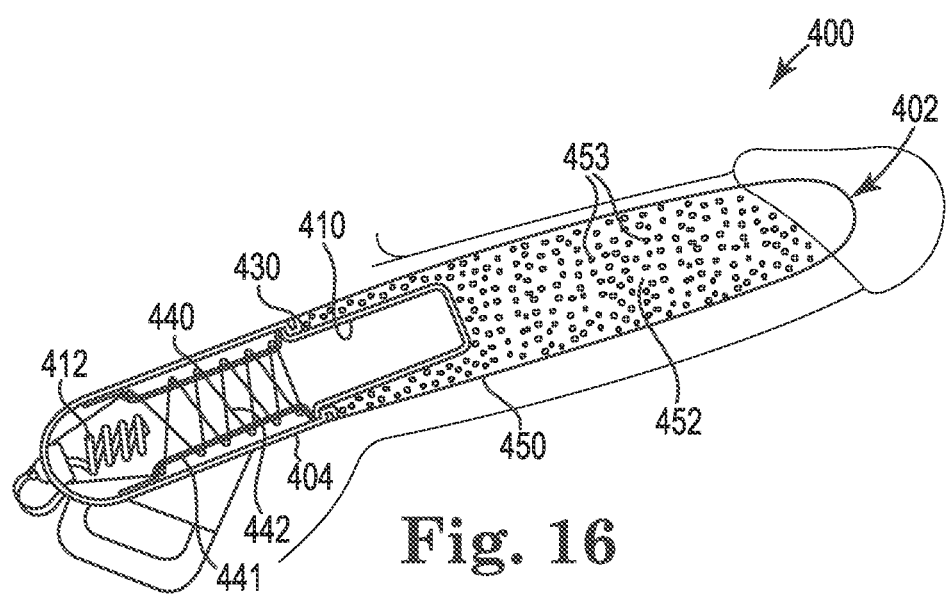
FIG. 16 is a side view of the implanted penile prosthesis of FIG. 15 in an erect state, where the prosthesis includes a tubular body containing an energy assembly.

FIG. 15 is a perspective view and FIG. 16 is a schematic side view of one embodiment of an implanted penile prosthetic 400 in a flaccid state. The implanted penile prosthetic 400 includes a pair 402 of implantable bodies and an energy assembly 404 coupled to a battery 406 by electrical connectors 408.

The implanted penile prosthetic 400 has fewer components than a three-piece penile implant device, and this beneficial configuration is realized using a phase-change fluid. The energy assembly 404 includes an expansion element in the form of a piston 410 that expands in response to a liquid phase change material (PCM) changing phase from a liquid to a gas. As an example, a heat source 412 is provided to heat a liquid hydrofluorocarbon 414 (HFC 414), and the heated HFC 414 changes phase to a gas that expands to push the piston 410 in a distal direction. Movement of the piston 410 in the distal direction increases the pressure in the inflatable bodies 402, which inflates or stiffens the penile implants 402.

In one embodiment, the heat source is an electric coil 412 that is powered by the battery 406. To inflate the implant, the user taps a pre-programmed and recognizable sequence onto a sensor 420. The sensor 420 is adapted to respond to the recognized sequence of taps and initiate the heating of the coil 412 and can be located along a variety of surfaces of the device. In one embodiment, the sensor 420 is adapted to respond to a wireless command to initiate heating of the coil.

The heated coil 412 drives the phase change of the HFC 414 from a liquid to a gas. The expanding gas causes the piston 410 to move or extend, and this expansion displaces a fixed volume of fluid 452 inside the implants 402 (i.e., pressurizes the fluid 452) to provide the penis of the user with an erection. The piston 410 eventually engages a piston stop 430 (See FIG. 16 and FIG. 18), which limits the distal travel of the piston 410. The expanded piston 410 provides the increase in pressure in the fluid 452, which provides the erection. The erection may be maintained by continuing to energize the heat source 412. The erection is maintained as long as the HFC is heated to the expanded state. To deflate, the user taps a pre-programmed sequence onto the sensor 420, shutting off the heater/coil 412, and the piston 410 retracts away from the piston stop 430.

Alternatively, the erection may be maintained by holding or supporting the piston 410 in the distal-most location of its travel, for example by a lock-out 440. In one embodiment, the lock-out 440 is mechanical and operates to retain the piston 410 in its expanded, distal position, which obviates continued high-energy consumption by the device to maintain the erect state, to thus preserve battery life.

In one embodiment, a lock-out 440 is provided by a corset having arms 441 or a spring 441. The arms 441 have a fixed proximal end and a movable distal end. A corset filament 442 is wrapped around the arms 441 to tighten the arms 441, which moves the distal end of the arms 441 inwards. Loosening of the corset filament 442 allows the distal end of the arms 441 to move outwards.

In this embodiment, after the piston 410 has traveled to the distal-most position and engages the piston stop 430, the proximal end of the arms 441 biases to an open position to prevent the piston 410 from retracting in the proximal direction, thus providing an effective lock-out 440 for movement of the piston 410. The lock-out 440 holds the piston 410 in place, which allows the energy source to be off to save power. When the power/energy source is off, the gas reverts to the lower volume liquid as the HFC cools (FIG. 16).

Figure 18:
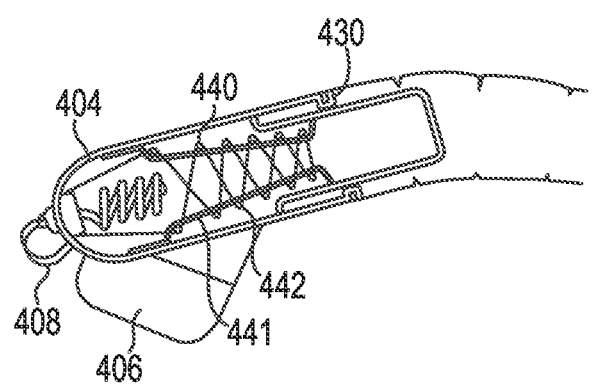
FIG. 18 is a schematic view of the implanted penile prosthesis of FIG. 15 transitioning to the erect state.

The lock-out 440 is shown having two fingers that slide within the piston 410 as the piston is displaced in the distal direction (FIG. 18). The lock-out 440 springs open to hold the piston 410 against the piston stop 430. A mechanical or other release decouples the lock-out 440 from the piston 410 to allow the piston 410 to retract. The retraction of the piston reduces pressure in the implanted cylinders, which become flaccid over a short period.

Tightening of the arms 441 disengages the lock-out 440. The mechanisms for disengaging the arms 441 includes: A) applying tension to the corset filament 442; B) forming one of the arms 441 or the corset filament 442 from a shape memory material so that the arms 441 or the filament 442 selectively transitions between the tightened state for the arms 441 (piston disengaged) and the loosened state of the arms 441 (piston engaged in by the lock-out 440) in response to thermal input; or C) wirelessly energizing and moving the arms 441 between the tightened state and the loosened state, for example, with an electro-mechanical system of moving the arms 441. One suitable arms 441 or spring for the lock-out 440 is formed of nickel-titanium (Ni—Ti) associated with the Naval Observatory labs, or NiTiNOL.

In one embodiment, the arms 441 lock-out feature provides the means for maintaining a hydrofluorocarbon-activated penile prosthesis in an erect state. In one embodiment, the lock-out feature provides the means for transitioning a hydrofluorocarbon-activated penile prosthesis selectively between a flaccid and an erect state.

Flaccidity is enhanced using a suitable filler, which limits the amount of fixed volume of liquid contained in the implant. In one embodiment, the energy source or battery 406 is recharged by wearing a magnetic garment overnight once every couple of weeks.

The pair 402 of implantable bodies includes a flexible distal portion 450 coupled to the energy assembly 404. The flexible distal portion 450 provides a sealed tubular body that in one embodiment contains a filler 453 or other material to occupy volume in the implantable body 402, which reduces the volume of saline or liquid in the distal portion 450. One suitable filler is a volume of gel beads or a bundle of strands. The filler 453 provides improved girth and bend angle for the flaccid implant, which is an advantage to some users.

The flexible distal portion 450 is preferably a thin-walled polymeric film, such as a polyurethane thin film. The flexible distal portion 450 is an expandable tubular structure. One suitable flexible body 194 is provided by the inflatable penile prosthesis cylinder sold under the trademark Titan® by Coloplast Corp., Minneapolis, Minn.

Figure 17:
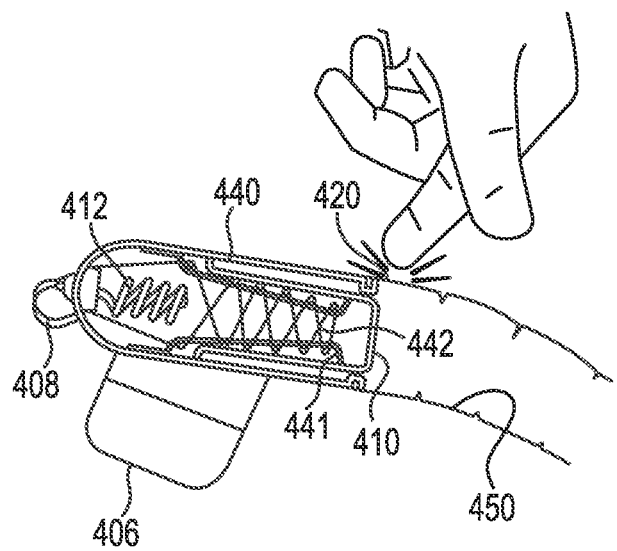
FIG. 17 is a schematic view of the implanted penile prosthesis of FIG. 15 being activated to move from the flaccid state to the erect state.

FIG. 17 is a schematic view of the implanted penile prosthesis 400 being activated to move from the flaccid state to the erect state. The HFC liquid 414 is contained within the piston 410 and exposed to the coil 412. The piston 410 is retracted in the proximal direction, which relieves pressure applied to the saline and filler 453 contained in the flexible distal portion 450.

FIG. 18 is a schematic view of the implanted penile prosthesis 400 transitioning to the erect state. The sensor 420 has sensed an appropriate input from the user and communicates the input to heat the coil 412. Heating of the coil 412 heats the liquid HFC 414, which changes the physical state of the liquid HFC 414 to a gaseous state. The gas expands and drives the piston 410 in a distal direction, which displaces both the liquid saline and the filler 453 inside the flexible distal portion 450. The piston 410 expands until the lock-out 430 is reached, which holds the piston 410 in place. As the liquid HFC 414 fully changes phase to gas, the pressure in the flexible distal portion 450 increases to a range between about 10-25 psi, which provides the implanted prosthesis 402 with the erect state.

During deflation, the expanded gaseous HFC 414 is allowed to cool, for example by removing heat applied by the coil 412. The cooling HFC returns to liquid form.

One suitable HFC is perfluorohexane represented as $C_6F_{14}$ and known as tetradecafluorohexane. Perfluorohexane is biologically inert and chemically stable.

In one embodiment, the energy assembly 404 contains an amount of perfluorohexane. Perfluorohexane, as well as other perfluorocarbons, offers excellent biocompatibility and no flammability issues. The perfluorohexane ($C_6F_{14}$) has a boiling point of 59 C and a 15 psig vapor temperature of 78 C. Thus, an implant containing the perfluorohexane will not experience a phase change solely due to the patient's body temperature. We calculate that a thin layer of film or insulation (about 1.5 mm of a polymer) will be sufficient to keep the surface temperature of the implanted device below 44 C. Moreover, energy costs are reasonable at 14 J/implanted cylinder, which can be supplied by a battery having an appropriate use life. One suitable battery is a 225 mAh battery available from EaglePicher, St. Louis, Mo. We expect that the implanted device will experience a sustained heatsink due to contact with the local tissue. For this reason, we have provided the lock-out 430 to hold the piston 410 in the expanded/erect position after the heat source 412 phase changes the HFC.

Table 1 below captures relevant calculations for start-up energy costs of a penile prosthesis utilizing a perfluorohexane energy assembly, and Table 2 presents data related to surface temperature power balance for the penile prosthesis.

TABLE 1

| Calculation | Values/Source | Answer |
| --- | --- | --- |
| Stroke × Diameter = Volume | $17 \times 10^{-3}$ m × $29 \times 10^{-3}$ m | $6.58 \times 10^{-6}$ m$^3$ |
| Gas temperature is the temperature for vapour pressure to equal 15 psi | From NIST webbook | 352K |
| Mols = (Pressure × volume)/ (Gas Constant × Temperature) | ($2 \times 10^5$ Pa × $6.58 \times 10^{-6}$ m$^3$ )/ 8.31 J · mol$^{-1}$ · K$^{-1}$ × 352K | $4.513 \times 10^{-4}$ Mol |
| Enthalpy of Vaporisation | From NIST Webbook | 31.4 kJ · Mol$^{-1}$ |
| Minimum Start Up Energy Cost = Mols × Enthalpy of Vaporisation | $4.513 \times 10^{-4}$ Mol × 31.4 kJ · Mol$^{-1}$ | 0.01417 kJ |

TABLE 2

| Calculation | Values/Source | Answer |
| --- | --- | --- |
| Surface Area | From CAD Sketch | $285 \times 10^{-6}$ m$^2$ |
| Internal Temperature | From NIST webbook (see Table 1a) | 352K |
| External Temperature | Assumed 37° C. body temperature and infinite heatsink relative to implant | 310.15K |
| Heat Transfer Coefficient | Assumed to be~convective heat transfer in water | 1000 W · m$^{-2}$ · K$^{-1}$ |

TABLE 2-continued

| Calculation | Values/Source | Answer |
|---|---|---|
| Heat flow from implant surface to body = (Heat Transfer Coefficient × Area)/ (Surface Temp − Body Temp) | (1000 W · m$^{-2}$ · K$^{-1}$ × 285 × 10$^{-6}$ m$^2$)/([ST] − 310.15K) | [Q] W |
| Thermal Resistance = Thickness/(Conductivity × Area) [for a 1.5 mm silicone covering] | 1.5 × 10$^{-3}$ m/ (0.2 W · m$^{-1}$ · K$^{-1}$ × 285 × 10$^{-6}$ m$^2$) | 26.31 K · W$^{-1}$ |
| Heat flow from core of implant to implant surface = (Internal Temp − Surface Temp)/ Thermal Resistance | (352K − [ST])/ 26.31K · W$^{-1}$ | [Q] W |
| Solve simultaneous equations for [ST] and [Q]: | | [Q] = 1.41 W [ST] = 315K = 41.8° C. |

In one embodiment, the penile prosthesis 400 includes an implantable body implantable into a corpus cavernosum of a penis, and a hydrofluorocarbon liquid sealed inside of a portion of the implantable body. The hydrofluorocarbon liquid is adapted to change to a gaseous state to provide the implantable body with a rigidity sufficient for penetrative intercourse.

In one embodiment, the penile prosthesis 400 includes a hydrofluorocarbon liquid sealed inside of a portion of an implantable body. The hydrofluorocarbon liquid is adapted to change to a gaseous state and inflate the implantable body.

In one embodiment, the hydrofluorocarbon liquid comprises perfluorohexane.

In one embodiment, the penile prosthesis 400 further includes a piston contained in a proximal end portion of the implantable body and a filler material contained within a distal end portion of the implantable body. The hydrofluorocarbon liquid in the gaseous state moves the piston in a distal direction to provide the implantable body with a rigidity sufficient for penetrative intercourse.

In one embodiment, the penile prosthesis 400 includes a tubular body implantable into a corpus cavernosum of a penis and an energy assembly. The energy assembly is coupled to a proximal end of the tubular body. The energy assembly includes a housing containing piston, a heating element, and a hydrofluorocarbon liquid sealed between an interior surface of the housing and the piston, with the hydrofluorocarbon exposed to the heating element. The heating element is adapted to heat the hydrofluorocarbon liquid to change the hydrofluorocarbon liquid to a gaseous state that expands to move the piston, thus inflating the tubular body and providing the penis with erection.

In one embodiment, the penile prosthesis 400 includes an implantable body implantable into a corpus cavernosum of a penis, and a separate gas-piston assembly is coupled to the implantable body by a flow path. The gas-piston assembly includes a hydrofluorocarbon liquid sealed inside the assembly. When the hydrofluorocarbon liquid changes to a gaseous state, the expansion of the gas moves through the flow path to provide the implantable body with a rigidity sufficient for penetrative intercourse. This embodiment decouples the implantable body from the expansion/energy source, which could provide the surgeon with options for implantation.

Figure 19A:
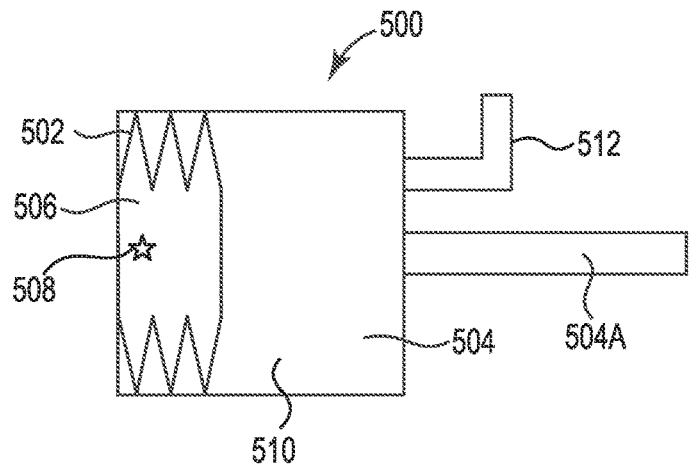
FIG. 19A is a side schematic view of a quiescent energy assembly of a penile prosthesis.

FIG. 19A is a side schematic view of one embodiment of an energy assembly 500 of a penile prosthesis, for example the penile prosthetic 400 of FIG. 15. The energy assembly is in a quiescent state.

The energy assembly 500 includes an expansion element in the form of a bellows 502 contained within a first portion 504 (or a chamber 504) of the prosthesis 400 (FIG. 15), a liquid phase change material (liquid PCM) 506 inside of the bellows 502, a heat source 508 inside of the bellows 502 and communicating with the liquid PCM 506, and a system liquid 510 contained inside of the first portion/chamber 504 and outside of the bellows 502. The first portion 504 or chamber 504 communicates with the inflatable portion 402 (FIG. 15) of the prosthesis through channel 504A and a separate fluid path 512 communicates with a reservoir containing a volume of the system liquid. The expansion element 502 or bellows 502 is sealed to contain the liquid PCM 506 and the heat source 508, which allows the portion/bellows 502 to contain the PCM even in its gaseous state.

The energy assembly 500 of the penile prosthesis 400 is adapted to cycle to inflate the prosthesis and create an erection. One example of the cycle includes heating the liquid PCM 506 with the heat source 508 to change the liquid PCM to a gaseous state. The PCM gas has a larger volume than the liquid PCM, which results in expansion of the bellows 502. The expanded bellows 502 occupies more space within the chamber 504 than the compressed bellows 502. The expansion of the bellows 502 displaces the system liquid 510 out of the chamber 504 and into the prosthesis through the channel 504A. After full expansion of the bellows 502, the heater is turned off and the PCM begins to cool. Dissipation of heat causes condensation of the PCM, which cools the PCM from its gaseous state back to its fluid state. During cooling, the bellows 502 contracts and forms a lower pressure inside of the chamber 504, which draws additional system liquid 510 from the reservoir through path 512 into the chamber 504. A set of valves ensures that fluid travels in one direction from the reservoir to the chamber 504, and from the chamber 504 to the prosthesis 400 to create an erection. The cycling on/off by the heat source 508 can be operated electronically with a controller that is programmed to run a sequence of on/off cycles. Alternatively, and less desirably, the user could repeatedly press a button coupled to the prosthesis.

The bellows 502 is sealed and configured to contain the liquid PCM and gaseous PCM. Suitable material for the bellows 502 includes metal coated films, or thin titanium metal bellows that are adapted to contain liquids and gases without leakage.

The first portion/chamber 504 of the prosthesis 400 communicates with the inflatable or expandable portion of the prosthesis through channel 504A. Like the prosthesis 400 described above, the energy assembly 500 is contained in the first portion 504, and a separate second portion of the prosthesis is configured as the flexible distal portion 450 (FIG. 16).

The liquid PCM 506 is a liquid that is adapted to change phase to a gas when heated or energized. Exemplary liquid PCM include the HFC 414, or the perfluorohexane ($C_6F_{14}$) described above. The liquid PCM generally has a boiling point above the normal body temperature of a human (37 C), for example about 59 C and with a 15 psig vapor temperature of 78 C. Thus, the prosthesis is stable while implanted in the human body and will not undesirably inflate to the erect state without an active command from the user.

The heat source 508 is like the heat source 412 described above and includes an electric coil that is powered by a battery. To inflate the implant, the user taps a pre-programmed and recognizable sequence onto a sensor of the prosthesis, or a command is sent wirelessly to the energy assembly 500. The sensor is adapted to recognize a sequence of taps and initiate the heating of the source 508. In one embodiment, the sensor responds to a wireless command to initiate heating of the source 508. The heated source 508 drives the phase change of the liquid PCM from a liquid to a gas.

Figure 19B:
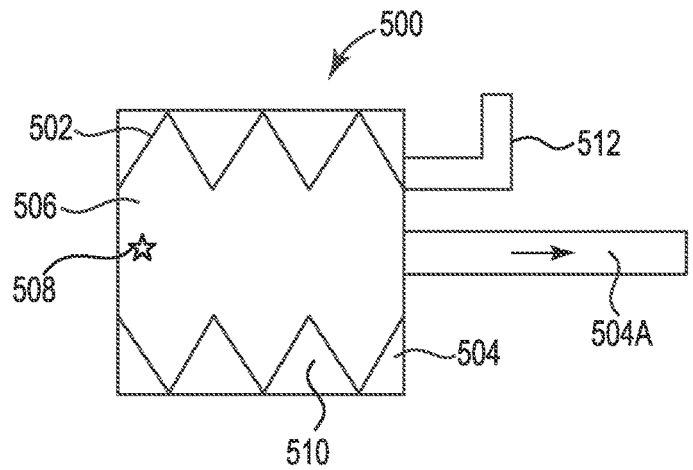
FIG. 19B is a side schematic view of an energized energy assembly of a penile prosthesis.

FIG. 19B is a side schematic view of the energy assembly 500 energized by the source 508 to expand the liquid PCM 506. Heating of the liquid PCM 506 changes its phase from liquid to gas, which expands the volume of the PCM, thus expanding the bellows 502. In this embodiment, the bellows or expansion element has a diameter approximately equal to the vertical and lateral dimension of the chamber 504. Expansion of the bellows 502 drives the system liquid 510 out of the chamber 504 through channel 504A to pressurize or expand or inflate the second portion of the prosthesis with the flexible distal portion 450. The system liquid 510 is aqueous, and one useful selection for liquid 510 is saline.

Figure 19C:
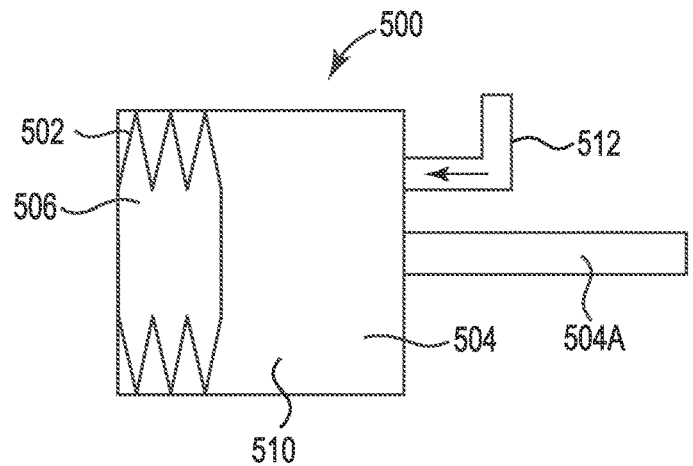
FIG. 19C is a side schematic view of a cooling energy assembly of a penile prosthesis.

FIG. 19C is a side schematic view of the energy assembly 510 in a cooling cycle. The heat source 508 is off and the PCM cools from the gas state to the liquid state. The phase change back to liquid reduces the volume of the PCM in the bellows 502, and the bellows 502 collapses. The contraction of the bellows 502 creates a local suction within the chamber 504, which draws additional system liquid 510 out of the reservoir through path 512 and into the chamber 504. With the heat source 508 off and the bellows 502 contracted, the energy assembly 500 returns to its initial state and is ready for a subsequent heat cycle to expand and pump liquid out of the chamber 504.

Figure 20:
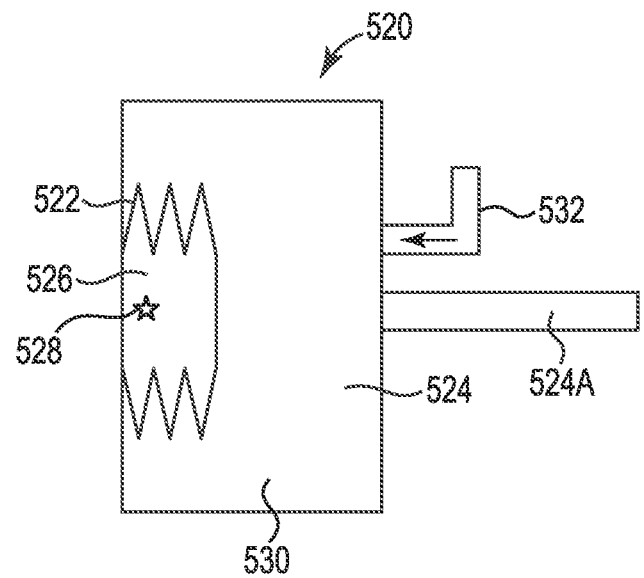
FIG. 20 is a side schematic view of an energy assembly of a penile prosthesis including a large heat sink.

FIG. 20 is a side schematic view of one embodiment of an energy assembly 520 including a large heat sink 524.

The energy assembly 520 includes an expansion element in the form of a bellows 522 contained within a first portion/chamber 524 of the prosthesis 400, a liquid phase change material (liquid PCM) 526 inside of the bellows 522, a heat source 528 inside of the bellows 522 and communicating with the liquid PCM 526, and a system liquid 530 contained inside of the first portion 524 and outside of the bellows 522. The first portion 524 or chamber 524 communicates with the inflatable portion of the prosthesis through channel 524A and a separate fluid path 532 communicates with a liquid reservoir.

Heat dissipation of the cooling PCM plays a role in the efficiency of the heat cycle. If the total heat is low enough, it may be possible to dissipate the heat generated by the phase change of the PCM to the tissue surrounding the implanted pump. However, a more efficient approach may be to use the system liquid 530 as a heat transfer medium. The system liquid 530 being aqueous can conduct heat away from the bellows 522 and carry the heat away to the prosthesis cylinder. This ensures better heat transfer over multiple cycles and reduces the chances of undesirably warming the tissue. The heat conduction provided by the system liquid 530 taking heat away from the bellows 522 and to the prosthesis cylinder can beneficially warm the glans penis. Users of inflatable penile prosthesis note that the implanted device can create a less than desired feeling of a cold glans penis, and the heat cycle and conduction of the energy into the prosthesis cylinder can be beneficially tuned to warm the glans penis.

The heat transfer rate away from the bellows 522 due to the phase change could be modified by changing the relative volume of the chamber 524 and bellows 522, as shown in FIG. 20. The generally larger chamber 524 will have a greater thermal capacity and could cool the PCM more rapidly. Internal vanes or fins (not shown) could also be incorporated within the chamber 524 to modify the mixing of inlet 532 and outlet 524 liquids so that heat transfer and cycling is optimal.

Figure 21:
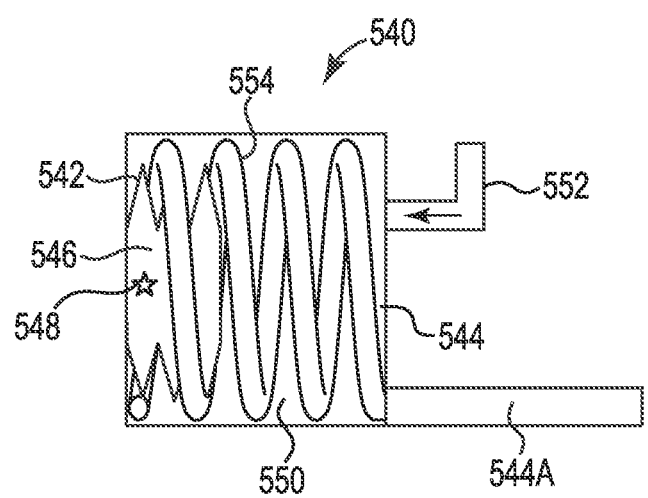
FIG. 21 is a side schematic view of an energy assembly of a penile prosthesis having a coiled outlet pipe.

FIG. 21 is a side schematic view of one embodiment of an energy assembly 540 having a coiled outlet pipe 554.

The energy assembly 540 includes a bellows 542 contained within a first portion/chamber 544 of the prosthesis 400, a liquid phase change material (liquid PCM) 546 inside of the bellows 542, a heat source 548 inside of the bellows 542 and communicating with the liquid PCM 546, and a system liquid 550 contained inside of the first portion 544 and outside of the bellows 542. The first portion 544 or chamber 544 includes a flow path through the coil 554 that communicates with the inflatable portion of the prosthesis through channel 544, and a separate fluid path 552 communicates with a liquid reservoir. The bellows 502 is an expansion element, generally, and other expansion elements include piston-like devices, expandable balloons, etc.

The coil 554 is inside of the chamber 544 and disposed around the bellows 542 such that a greater percentage of system heat is convected away with each cycle of the energy assembly 540. In one embodiment, the coil 554 is placed around the expansion element 542 or bellows 542, where the coil 554 is adapted to dissipate the heat generated by the energy assembly by drawing a portion of the system liquid 550 from the first portion 544 and delivering to the inflatable portion(s) of the prosthesis. The energy assembly 540 having the coil 554 provides an efficient way to dissipate heat during the cycles to beneficially avoid a local warming of the tissues around the implant and to potentially warm the prosthesis near the glans penis.

Although specific embodiments have been illustrated and described in this disclosure, it will be appreciated by those of ordinary skill in the art that a variety of alternate and/or equivalent implementations may be substituted for the specific embodiments shown and described without departing from the scope of this disclosure. This application is intended to cover any adaptations or variations of the above-disclosed medical devices. Therefore, it is intended that this invention is limited only by the claims and their equivalents.

What is claimed is:

1. A penile prosthesis implantable into a corpus cavernosum of a penis, the penile prosthesis comprising:
 an energy assembly contained within the penile prosthesis, the energy assembly comprising a heating element and a liquid phase change material (PCM) sealed within an expansion element, with the liquid PCM exposed to the heating element;
 a distal portion coupled with the energy assembly, with the distal portion containing a liquid;
 wherein the heating element is adapted to heat the liquid PCM to a gaseous state that expands to move the expansion element in a distal direction, thus increasing a pressure in the liquid in the distal portion thus providing the penile prosthesis with erection;

wherein the energy assembly is contained inside of a chamber, with the chamber containing a first volume of system liquid, and the expansion element communicates with the first volume of system liquid, with the penile prosthesis further comprising:

a reservoir coupled to the chamber, with the reservoir containing a second volume of system liquid;

a channel communicating between the chamber and the distal portion;

wherein movement of the expansion element in the distal direction displaces a portion of the first volume of system liquid through the channel and into the distal portion to pressurize the liquid in the distal portion, thus providing the penile prosthesis with erection; and a coil placed around the expansion element, with the coil adapted to dissipate heat generated by the energy assembly.

2. The penile prosthesis of claim 1, wherein the heating element comprises an electric coil that is coupled to a battery.

3. The penile prosthesis of claim 1, wherein the liquid PCM is perfluorohexane $C_6F_{14}$.

4. The penile prosthesis of claim 1, wherein the liquid PCM has a boiling point of 59 C.

5. The penile prosthesis of claim 1, wherein the liquid PCM has a 15 psig vapor temperature of 78 C.

6. The penile prosthesis of claim 1, wherein the expansion element is a piston.

7. The penile prosthesis of claim 6, further comprising:
a piston stop adapted to limit travel of the piston in the distal direction.

8. The penile prosthesis of claim 6, further comprising:
a lock-out adapted to retain the piston at an expanded distal position to maintain the erection as the PCM in the gaseous state returns to the PCM liquid.

9. The penile prosthesis of claim 1, wherein the expansion element is a bellows.

10. The penile prosthesis of claim 1, wherein the distal portion is a sealed distal portion sealed to contain a filler immersed in the liquid, and movement of the expansion element in the distal direction pushes into the sealed distal portion to increase the pressure in the liquid to provide the penile prosthesis with erection.

11. The penile prosthesis of claim 1, wherein the distal portion is a sealed distal portion sealed to contain a gel suspended in the liquid, and movement of the expansion element in the distal direction pushes into the sealed distal portion to increase the pressure in the liquid to provide the penile prosthesis with erection.

12. The penile prosthesis of claim 1, wherein the penile prosthesis further comprises a rigid first portion connected to the distal portion, and the energy assembly is contained inside of the rigid first portion of the penile prosthesis.

13. The penile prosthesis of claim 1, wherein a lateral dimension of the chamber is approximately equal to a diameter of the expansion element.

14. A penile prosthesis comprising:
a tubular body comprising a distal portion coupled to a proximal portion, where the distal portion contains a fluid and the proximal portion comprises an energy assembly;
wherein the energy assembly encloses a heating element and a hydrofluorocarbon liquid sealed inside of an expansion element, with the hydrofluorocarbon exposed to the heating element;
wherein changing a state of the hydrofluorocarbon liquid to a gaseous state expands the expansion element in a distal direction to pressurize the fluid in the distal portion, thus providing the penile prosthesis with erection,
wherein the expansion element is a bellows and the proximal portion comprises a chamber containing system liquid that surrounds the bellows, with the penile prosthesis further comprising:
a reservoir coupled to the chamber; and
a port communication between the chamber and the distal portion;
wherein expansion of the expansion element in the distal direction displaces a portion of the system liquid out of the chamber and through the port and into the distal portion to pressurize the fluid in the distal portion, thus providing the penile prosthesis with erection.

15. The penile prosthesis of claim 14, wherein the expansion element is a piston and the distal portion is sealed with a barrier between the proximal portion and the distal portion, with the fluid sealed inside of the distal portion;
wherein, expansion of the expansion element pushes the piston into the barrier to pressurize the fluid sealed in the distal portion.

16. The penile prosthesis of claim 14, further comprising:
a battery electrically coupled to the heating element.

17. The penile prosthesis of claim 14, wherein the distal portion is sealed to contain a filler in the fluid, and the filler is configured to increase a girth of the distal portion when the penile prosthesis is flaccid.

18. A penile prosthesis comprising:
a tubular body comprising a distal portion coupled to a proximal portion, where the distal portion contains a fluid and the proximal portion comprises an energy assembly;
wherein the energy assembly encloses a heating element and a hydrofluorocarbon liquid sealed inside of an expansion element, with the hydrofluorocarbon exposed to the heating element;
wherein changing a state of the hydrofluorocarbon liquid to a gaseous state expands the expansion element in a distal direction to pressurize the fluid in the distal portion, thus providing the penile prosthesis with erection;
wherein the distal portion is sealed to contain a filler in the fluid, and the filler is configured to increase a girth of the distal portion when the penile prosthesis is flaccid.

19. A penile prosthesis implantable into a penis, the penile prosthesis comprising:
a pair of implantable bodies including a first device implantable into a first corpus cavernosum of the penis and a separate second device implantable into a second corpus cavernosum of the penis, with each of the first device and the second device comprising:
a proximal portion implantable into a crus of a penis;
an energy assembly contained within the proximal portion, with the energy assembly comprising a heating element and a liquid phase change material (PCM) sealed within an expansion element, with the liquid PCM exposed to the heating element; and
a distal portion coupled to the proximal portion, with the distal portion containing a liquid;
wherein the heating element within the proximal portion is adapted to heat the liquid PCM to a gaseous state that expands to move the expansion element in a distal direction, thus increasing a pressure in the liquid in the distal portion and providing the penile prosthesis with erection.

20. The penile prosthesis of claim 19, wherein the heating element comprises a battery-powered electric coil.

21. The penile prosthesis of claim 19, wherein the heating element comprises an electric coil that is coupled to a battery by electrical connectors, with the battery located external to the proximal portion.

22. The penile prosthesis of claim 19, wherein the expansion element is a piston.

23. The penile prosthesis of claim 22, further comprising:
a piston stop adapted to limit travel of the piston in the distal direction.

24. The penile prosthesis of claim 22, further comprising:
a lock-out adapted to retain the piston at an expanded distal position to maintain the erection as the PCM in the gaseous state returns to the liquid PCM.

* * * * *

UNITED STATES PATENT AND TRADEMARK OFFICE
CERTIFICATE OF CORRECTION

PATENT NO. : 11,819,412 B2
APPLICATION NO. : 17/166062
DATED : November 21, 2023
INVENTOR(S) : Frederick William Hamlin et al.

Page 1 of 1

It is certified that error appears in the above-identified patent and that said Letters Patent is hereby corrected as shown below:

In the Claims

Claim 14 at Column 22, Line 13: "a port communication" should read "a port communicating"

Signed and Sealed this
Twentieth Day of February, 2024

Katherine Kelly Vidal
*Director of the United States Patent and Trademark Office*